US012781170B2

(12) United States Patent
Hafenbradl et al.

(10) Patent No.: US 12,781,170 B2
(45) Date of Patent: Nov. 3, 2026

(54) REACTOR PLANT AND METHOD TO CONTROL PERFORMANCE

(71) Applicant: Electrochaea GmbH, Planegg (DE)

(72) Inventors: Doris Hafenbradl, Pullach (DE); Matteo Cociancich, Munich (DE)

(73) Assignee: Electrochaea GmbH, Planegg (DE)

( * ) Notice: Subject to any disclaimer, the term of this patent is extended or adjusted under 35 U.S.C. 154(b) by 0 days.

(21) Appl. No.: 18/563,504

(22) PCT Filed: May 25, 2022

(86) PCT No.: PCT/EP2022/064189
§ 371 (c)(1),
(2) Date: Nov. 22, 2023

(87) PCT Pub. No.: WO2022/248545
PCT Pub. Date: Dec. 1, 2022

(65) Prior Publication Data

US 2024/0240127 A1 Jul. 18, 2024

(30) Foreign Application Priority Data

May 27, 2021 (DE) ..................... 10 2021 113 678.4

(51) Int. Cl.
*C12M 1/00* (2006.01)
*C12M 1/36* (2006.01)

(52) U.S. Cl.
CPC ............ *C12M 23/58* (2013.01); *C12M 41/48* (2013.01)

(58) Field of Classification Search
CPC ...... C12M 23/58; C12M 41/48; C12M 21/18; C12M 29/00; G05B 19/41865
See application file for complete search history.

(56) References Cited

U.S. PATENT DOCUMENTS 10,662,449 B2 5/2020 Kano et al.
2008/0288089 A1* 11/2008 Pettus ................ G05B 19/4184 700/9
2011/0091955 A1* 4/2011 Constantz ................ F23J 15/04 435/177

(Continued)

FOREIGN PATENT DOCUMENTS

| | | |
|---|---|---|
| CN | 201442939 U | 4/2010 |
| EP | 0253199 A2 | 1/1988 |

OTHER PUBLICATIONS

International Search Report and Written Opinion for International Application No. PCT/EP2022/064189, mailed Sep. 23, 2022 (8 pages).

(Continued)

*Primary Examiner* — Michael L Hobbs
(74) *Attorney, Agent, or Firm* — Clark & Elbing LLP

(57) ABSTRACT

A reactor plant according to the present invention comprises two or more reactors, connected in parallel to each other. Each of the two or more reactors comprise a load sensitive catalyst. The reactor plant is characterized by its capability and corresponding control systems to periodically permutate the operation load in the individual reactors. Particularly in a situation, when the plant operates with reduced operation load, the two or more reactors are configured to periodically permutate their operation load.

7 Claims, 3 Drawing Sheets

(56) References Cited

U.S. PATENT DOCUMENTS

Figure 1:
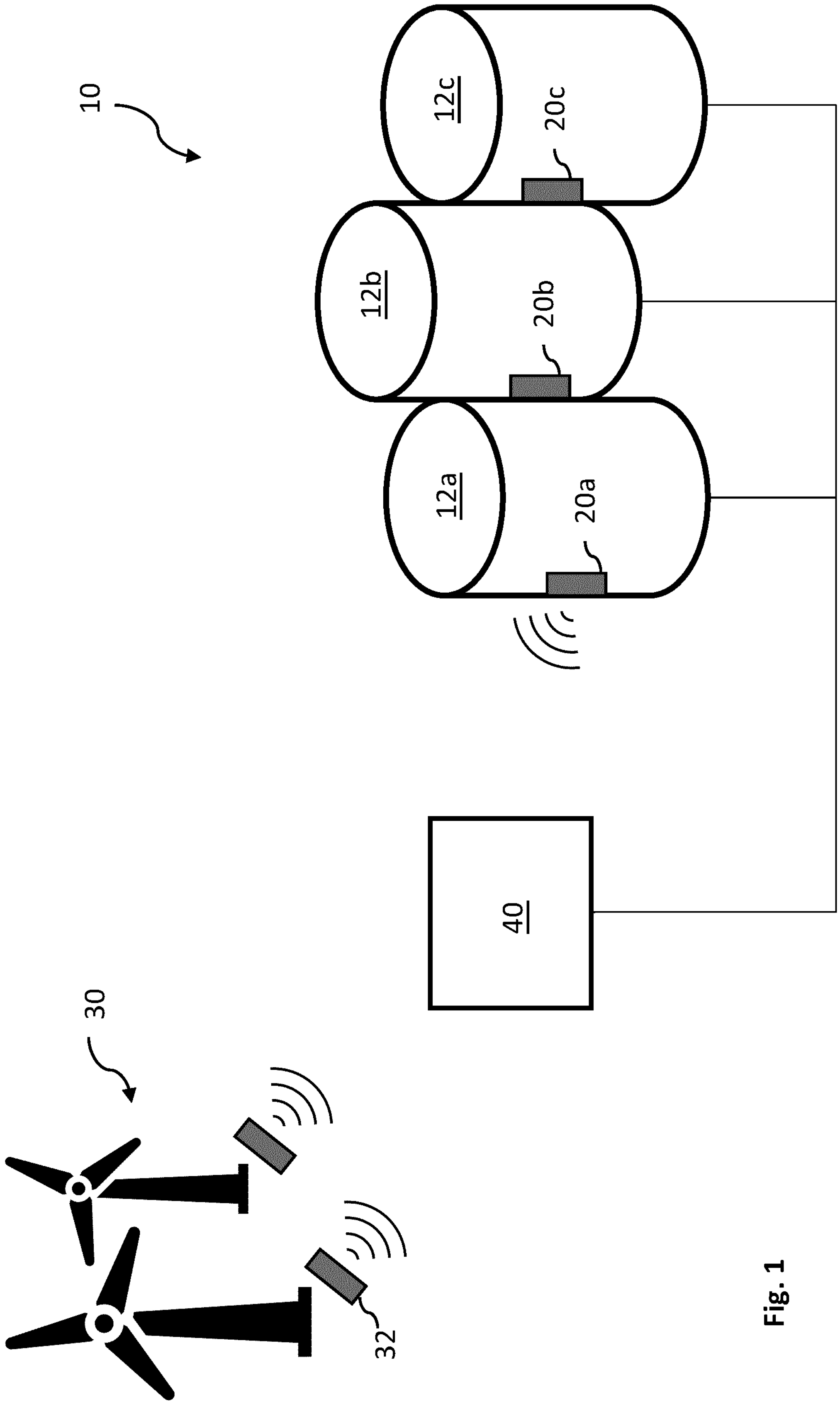

| | | | | |
|---|---|---|---|---|
| 2012/0122195 | A1* | 5/2012 | Fradette | B01D 53/96 435/266 |
| 2015/0104782 | A1* | 4/2015 | Madore | C12M 25/18 435/180 |
| 2019/0332101 | A1* | 10/2019 | Castillo Castillo | G05B 19/41875 |

OTHER PUBLICATIONS

International Preliminary Report on Patentability Chapter 2 for International Patent Application No. PCT/EP2022/064189, issued Nov. 27, 2023 (5 pages).

* cited by examiner

Reduced operation load plant 50%

| | Operation load<br>Operation load reactors in % of optimal load capacity of plant | |
|---|---|---|
| | **Reactor 1** | **Reactor 2** |
| **t=1** | 50% | 0% |
| **t=2** | 0% | 50% |

Fig. 2a

Reduced operation load plant 75%

| | Operation load<br>Operation load reactors in % of optimal load capacity of plant | |
|---|---|---|
| | **Reactor 1** | **Reactor 2** |
| **t=1** | 50% | 25% |
| **t=2** | 25% | 50% |

Fig. 2b

Reduced operation load plant 50%

| | **Operation load**<br>Operation load reactors in % of optimal load capacity of plant | | |
|---|---|---|---|
| | **Reactor 1** | **Reactor 2** | **Reactor 3** |
| **t=1** | 33% | 17% | 0% |
| **t=2** | 0% | 33% | 17% |
| **t=3** | 17% | 0% | 33% |

Fig. 3a

Reduced operation load plant 75%

| | **Operation load**<br>Operation load reactors in % of optimal load capacity of plant | | |
|---|---|---|---|
| | **Reactor 1** | **Reactor 2** | **Reactor 3** |
| **t=1** | 33% | 33% | 9% |
| **t=2** | 9% | 33% | 33% |
| **t=3** | 33% | 9% | 33% |

Fig. 3b

REACTOR PLANT AND METHOD TO CONTROL PERFORMANCE

The present application relates to an arrangement of two or more reactors, e.g. fermentation reactors in a reactor plant to guarantee long-lasting and optimised efficiency.

Reactor plants comprising more than one reactor, e.g. two or more reactors are widely known and used in many technical fields, like the chemical industry or biotechnology, such as e.g. bioreactor plants or microbial fermentation plants.

Focusing on bioreactor plants, such reactors typically employ a catalyst, which converts or synthesizes from suitable starting materials a desired product. In this invention this is defined as a "reaction". To achieve a reaction the catalyst requires energy or in the case of a biocatalyst it requires energy and at least one substrate. In the context of the present invention, the term "biocatalyst" is defined as and comprises any hydrogenotrophic methanogen suitable to be used alone or in co-culture in a methanation process.

Furthermore, it is established knowledge that biocatalysts require the right balance and quantity of energy and substrate(s) to achieve substantially optimal (e.g. efficient) reactions. The term "load" in this invention encompasses both energy and substrate(s) together and/or singularly fed to the biocatalyst, and serves as a general term for describing the compounds needed for maintenance and reaction. Hence a biocatalyst requires a right balance and amount of load (i.e. an "optimal load") to achieve substantially optimal and efficient reactions.

Reactors comprise the catalyst and hence reactors can be described by its "optimal load capacity", this being the optimal amount of load the catalyst can and/or should be fed with to obtain substantially optimal reactions.

When the biocatalyst is achieving substantially optimal reactions by being fed the optimal load it is defined as being "adapted to high load" or as being in "high load adaptation". When instead the biocatalyst is confronted with less-than-optimal load the reactions of the biocatalyst are less efficient, then the biocatalyst adapts to "low load" or is "adapted to low loads". Biocatalyst for which their reaction efficiency changes depending on the load changes (e.g. the amount of load it is fed) are defined as being "sensitive to load changes".

The terminology "adapted" or "adaptation" is accurate. A biocatalyst indeed needs to adapt to new feeding/load regimes and requires time to adapt to new situation. This means in particular that when a biocatalyst experience changes in load it maintains its state of adaptation (e.g. high load adaptation or low-load adaptation) for some amount of time. The amount of time it remains in such state is given by the characteristics or individual properties of the specific (bio)catalyst. This period is defined as "latency period" and describes the timeframe for which a catalyst can remain adapted to high load adaptation even without receiving any load.

The time that a (bio)catalyst requires to adapt to a different feeding regime, such as a high load regime after having been in a state of low load adaptation e.g. due to disturbances in the load supply e.g. shortages of energy and/or of substrate or complete shutdown of a reactor is defined as the "ramp-up time" of a reactor.

A reactor or a reactor plant operates with an "operation load". The operation load being the load with which the biocatalysts is fed during standard operation of the reactor. An operation load of a reactor is hence the amount of load with which the biocatalyst in the reactor is fed. The sum of the operation loads of all reactors in the reactor plant at a given timeframe corresponds to the operation load of the plant at such given timeframe.

Although much research has been put in ameliorating reactor plants, plants of the prior art still envisage several disadvantages.

In particular, ramping up a reactor of the prior art after the reactor experienced disturbances in its load availability, requires high amounts of energy. This combined with the lengthy ramp up time of the biocatalyst once the disturbance is cleared, renders the reaction process rather inefficient.

Such disturbances in load and especially if load is considered to be or be related to energy occur in situations where the energy source is a renewable energy source (e.g. wind and/or solar energy). A reactor with an inconsistent, intermittent energy source may therefore require other available sources of energy or energy storage systems to compensate any potentially occurring load shortages. Use of energy storage systems, however, requires more complex plant architecture and higher installation costs as well as higher maintenance efforts.

In case of solar energy, it might be necessary to use stored energy during the night or on cloudy days. In periods with little sunlight, such as winter, it might become necessary to add or make available other energy sources, which might not be renewable. Hence increasing the carbon footprint of such plant. Similar issues arise with other renewable energy forms, such as e.g. wind power during times of reduced wind activity.

It is therefore the aim of the present system to provide a reactor plant, which solves some of the above problems.

This aim is solved by a rector system as described herein, including advantageous embodiments of the invention. A method and a computer implemented method to operate such a system is also provided.

A reactor plant according to the present invention comprises two or more reactors, e.g. three, four, five, six, seven, eight, nine or ten reactors. Also, rector plants with more than ten reactors are envisaged. The two or more reactors are connected (in parallel) to each other. Each of the two or more reactors are suitable to hold a chemical or biochemical reaction and each reactor comprises a load sensitive catalyst.

Each reactor of the two or more reactors has an optimal reactor load capacity, hence an ideal quantity of load, which must be fed to the reactor to obtain substantial optimal and efficient reactions in suitable cases catalysed by the load sensitive biocatalyst. The sum of the optimal reactor load capacity of the two or more reactors correspond to the overall optimal load capacity of the reactor plant. The overall optimal load capacity of the plant is hence the cumulated amount of load required for all reactors in the plant to experience substantial optimal and efficient reactions.

The reactor plant is configured to operate with an operation load. The operation load of the reactor plant can be its optimal load capacity or a reduced operation load.

Additionally, the operational load of the reactor plant can also be higher than the optimal load. In order to allow accommodating expected, expectable or unexpected peaks of electricity the reactor plant may be constructed and designed in a dimension that would be described as a higher percentage than 100% optimal load. Such so called "overdesign" allows the plant to normally work under optimal operational load capacity, and still it is envisaged that the same reactor plant can accommodate higher operational loads if exceptionally peaks of electricity need to be or should be addressed. Such overdesign may typically be addressed while planning the reactor plant and might involve extra investment, which however leads to a reactor plant with an inbuilt safety margin and thus being even better equipped to address typical imbalances of renewal energy exploitation and thus, additionally allows to stabilize and advantageously support the electricity grid.

Accordingly, the two or more reactors of a reactor plant are configured to operate with an operation load, wherein the combined operation load with which the two or more reactors operate is substantially equal to the operation load of the reactor plant.

The reactor plant is characterized by its capability and corresponding control systems to periodically permutate the operation load in the individual reactors. Particularly in a situation, when the plant operates with reduced operation load, the two or more reactors are configured to periodically permutate their operation load. In this case the timeframe of permutation is depending on the characteristics of the catalyst.

According to some embodiments of the invention the load sensitive catalyst is a biocatalyst. According to further embodiments the biocatalyst is of the family of Archaea. Archaea are sensitive to load changes, hence to the quantity of load they are fed with. Archaea however have the advantage of being rather unsensitive to lower loads for extended periods of up to 10 hours, meaning that Archaea are capable to maintain their metabolism in high load adaptation mode even, or particularly, during periods of load disturbance, if such periods of disturbances have an average duration of less than 10 hours.

The great advantage of the present invention, as will disclosed more in detail here below, is that the catalyst is maintained in high load adaptation even during periods in which the available load for the individual reactor would suggest a reduced efficiency and should not permit efficient reactions of the biocatalyst.

In particular, it is the advantage of the invention that due to the permutations of loads the disturbance periods, i.e. the periods of reduced or no load input to the reactor can be substantially longer than the periods in which the catalyst remains at high load adaptation.

This guarantees optimal output in terms of quantity and quality of the reaction product and hence of the plant also during periods of low load availability.

The optimal load capacity of the reactor plant is defined as being ca. 100%. The optimal load capacity of the two or more reactors is given in proportion to the 100% of the optimal load capacity of the plant. If for example the plant comprises two reactors, the optimal load capacity of the two reactors may be configured as 50% of the optimal load capacity of the plant (ca. 100%), each.

Other combinations of the distribution of the optimal reactor feeding capacities of the two or more reactors are also envisaged. The distribution among two reactors may for example be any combination from ca. 5%-ca. 95% to ca. 55%-ca. 45%.

According to an embodiment of the invention the optimal load capacity of the individual reactors of a reactor plant is evenly distributed. In a plant with three reactors, this would result for each reactor in an optimal load capacity of ca. 33% of the 100% load capacity of the plant.

Accordingly, wherever in this invention it is stated that one of the reactors "operates at ca. 33%", the reactor is fed with ca. 33% of the optimal load capacity of the plant. This means that ca. 33% of load for the whole plant is fed to that specific reactor and for this individual reactor it is considered the optimal load.

According to the invention the reactor plant is configured to operate with an operation load, the operation load being either its optimal load capacity or a reduced operation load capacity.

When a plant operates with its optimal load capacity it is fed with its maximal amount of load—energy and/or substrate(s)—needed for substantial optimal reactions for all individual reactors. Hence all reactors of the plant operate substantially with their optimal load capacity. While this seems to be the ideal and most wishful situation, reality only rarely allows such ideal exploitation of reactor plant.

The inventors of the present invention provide a stunning teaching to adapt the reactor plant to reality and particularly to situations of reduced operation load availability, as well as to situations of unexpected overload peaks.

According to the present invention, the term "reduced operation load" means that the plant or at least one reactor is fed with a reduced load, e.g. less than the respective optimal load capacity of an individual reactor. The reduced operation load of a reactor is hence defined in relation to the optimal load capacity of the plant (e.g. ca. 100%).

Reduced operation loads can for example be. ca. 90%, ca. 80%, ca. 70%, ca. 60%, ca. 50%, ca. 40%, ca. 30%, ca. 20%, ca. 10% or less then the optimal load capacity (e.g. 100%) of the plant. Reduced operation loads are not limited to these round numbers and can be any load less than the optimal load capacity e.g. ca. 95%, ca. 85%, ca. 75%, ca. 65%, ca. 55%, ca. 45%, ca. 35%, ca. 25%, ca. 15% or ca. 5%.

In any typically known reactors, if for example the plant comprises two reactors, each reactor may have optimal load capacity of ca. 50%. If, the plant only operates with a ca. 50% reduced operation load, the two reactors would be understood to operate with ca. 25% reduced operation load each. In this way both reactors would operate only with half of their optimal load capacity.

In contrast to this and according to the present invention the individual reactors are periodically permutated in a way that always one reactor operates with ca. 50% load (i.e. it's optimal load capacity) while the second reactor operates with ca. 0% load, e.g. it is off.

Due to such permutation schedule, which will be explained in more details and including many more variables below, a reactor plant can adjust to almost each and every variation of reduced operation load, without the need of a ramp-up-time for the bio catalyst. Consequentially, the efficiency of the reactor plant is at all times ideal and optimal adapted to the available load.

There are many reasons for the plant to be fed with a reduced operation load. One reason is load scarcity. Due to non-constant, intermittent, energy input from external energy sources, it might for example be necessary to decrease the load fed to the plant. This might be case where the received energy is supplied entirely through renewable energies and the source of the renewable energy is limited (e.g. period of little winds, cloudy periods, winter month). In such situation the energy available for operation load is lower than the optimal load.

Load-following might also be a reason for a reduced operation load. For example, less energy might be required as an output of the plant, and hence to minimizes energy waste, the reactor plant is operated with a reduced operation load.

Other reasons might encompass financial reasons, such as higher energy prices during a period of the day, rendering it advantageous to only have a reduced operation load during that period, or global energy shortages and geopolitical energy crises.

The two or more reactors of the plant are connected in parallel to each other, meaning that they can operate simultaneously to each other. The two or more reactors can also be operated independently from each other, meaning that the operation load with which each reactor operates is set independently and individually.

This offers high operating flexibility through independent controlling of individual reactors. It also generates an overall higher output as maintenance work or reparation work can be done to singular reactor without having to shut down the whole plant.

The plant is further characterised in that during a period of reduced operation load of the plant, the two and more reactors are configured to periodically permutate their respective operation loads, wherein the period depends on the catalyst used in the reactors.

In a plant with three reactors, a permutation of loads results in the first reactor being fed with the amount of load that the second reactor was being fed. The second reactor being fed with the amount of load that the third reactor was being fed with and the third reactor being fed with the amount of load that the first reactor was being fed with. A further permutation would permutate the loads further. The present invention is however not limited to any specific permutation order.

The overall operation load of the plant remains unaltered after a load permutation and only the distribution of operation loads of the two or more reactor in the plant changes.

In particular, according to a further embodiment of the current invention, the timing of the permutations follows a permutation schedule. This schedule is set according to the metabolic characteristics of the catalyst and is such that the catalyst in all reactors remains adapted to high loads even during load disturbances.

Notable and surprising advantages go along with the permutation of loads according to the present invention. It guarantees uniform usage of the reactors at different operation loads resulting in a more homogenous wearing of the two or more reactors of the plant. A homogeneous wearing means that maintenance work can be better predicted and better spread out in time. It also minimizes probability of breakage of the singular reactors and hence guarantees a safer working environment.

The periodical permutation of the loads of the reactors during a reduced operation load period of the plant is particularly advantageous when load sensitive catalyst are being used. According to one embodiment of the invention a load sensitive catalyst is used. According to further embodiments this load sensitive catalyst is selected from the group of Archaea and one or more hydrogenotrophic methanogen.

The permutation of loads results in a substantially constant optimal reaction of the reactor plant, even during load disturbances and thus, guarantees a particularly efficient reactions, while using less externally needed energy (load).

A plant comprising a first and a second reactor each having 50% of substantial optimal load capacity. When the plant is operating at a reduced operation load of 50%, according to one embodiment, the first reactor is then configured to operate with said reduced operation load of 50% (hence at its optimal load capacity) while the second reactor is fed with 0% load.

The reactions of the first reactor are hence substantially optimal and the catalyst is ideally adapted to the high load. The catalyst of the second reactor, although not receiving any load, remains adapted to high load during its latency period. During this period, although no reaction is ongoing in the second reactor, the capability of the catalyst remains unchanged. After the predefined period of permutation, the load feeding of the two reactors is interchanged and the previously first reactor receives no load while the previously second reactor receives the reduced operation load of 50% (its optimal load capacity) and thus performs immediately substantial optimal reactions with a catalyst still ideally adapted to the high load. Substantially no ramping-up time is needed. Hence both reactors are experiencing substantially optimal reactions in response to the operational load as long as the catalyst is kept adapted to high load.

Archaea for example can stay adapted to high load for an average of about 10 hours without receiving any load. After about 10 hours the Archaea adapts to low load and metabolic activities are accordingly adjusted. Consequentially, this means after about 10 hours in which the load disturbance occurred Archaea typically require additional amount of energy and time to ramp up again and react substantially optimal once the load disturbance has disappeared.

By permutating the loads of the reactors before such exemplary 10 hours period (here in the example for Archaea) an adaptation of the catalyst to low load in the second reactor can be avoided. After such permutation the first reactor is fed with 0% load and the second reactor is fed with its substantially optimal load capacity (ca. 50% of the operational load of the plant).

The catalyst of the second reactor hence stays also adapted to high load because it receives again substantially optimal load. The catalyst of the first reactor, although not receiving any load, remains adapted to high load and as did the second reactor before permutations and maintains its metabolic characteristics. According to the invention and in order to maintain the advantages of the invention the next permutation should be effected before the exemplary 10 hours period is over again.

According to the present invention the catalyst of all reactors, if possible, is therefore kept continuously adapted to high loads. The time period for performing the periodic permutations depends on the latency period of the catalyst, on the amount of load available for the plant and the number of reactors as well as their optimal load capacity.

The advantages are manifold. Apart from substantially continuous operation at high loads and hence an increase in production, the energy consumption is reduced, and production is maximized by the minimization of ramp up times and by avoiding additional energy to bring the catalyst into a high load adaptation. It is extremely advantageous, as even with non-optimal conditions, the system can be kept substantially operating with optimal reaction and highest efficiency.

Its efficiency becomes evident, if the ramp up time is compared to a reactor in which the catalyst returned to a low load adaptation due to an extended period of reduced load availability. The ramp up time is in such situation usually around 30 minutes. With the current invention, the ramp up time required for the reactor receiving optimal load after a period with zero load, but with the catalyst adapted to high load is ca. 4% per second, meaning a ramp up rate of ca. 25 seconds in total to produce again substantially optimal reactions. The ramp up rate is improved and kept up to ca. 95%-ca. 99% more efficient than in any prior art reactor plant.

Furthermore, the alternate and nested operation secures continuous output of the plant over the whole period as the ramp down rate of one reactor is compensated by the ramp up time of the other reactor. During permutation, the reliable flow transition between reactors, thus guarantees a constant output in terms of quantity and in terms of quality. By requiring less energy, the plants of, the present invention are also more environmentally friendly.

According to some embodiments, when operating with reduced operation load, the plant is configured to operate with the minimum number of reactors possible at that reduced operation load. Consequently, the plant is configured to maintain, if possible, always at least one reactor at operation with its optimal reactor load capacity (hence feeding at least one reactor with its optimal amount of load). This is of course only possible when the load fed to the plant during reduced operation load is at least equal or higher than the optimal reactor load capacity of at least one of the reactors.

If, for example, the plant comprises three reactors having an optimal reactor load capacity of ca. 33% each, and the plant must operate with a reduced operation load of ca. 50%, then at least one reactor of the three reactors is fed always ca. 33% operation load. A further reactor operates with ca. 17% (to achieve the ca. 50% reduced operation load of the plant) and the last reactor is maintained with 0% load.

After each permutation a different reactor is fed with 33%, 17% and 0% load, respectively and hence always at least one reactor operates at its optimal capacity, irrespective of the permutation. This means in particularly that if possible, during reduced operation load of the plant at least one reactor is kept with no load. According to some embodiments, if the reduced operation load of the plant and the number of reactors so permits, at least one reactor will always receive no load, during reduced operation load of the plant.

According to even further embodiments of the present invention the two or more reactors are reactor cells in a main reactor. In particular, the two or more reactors of the plant do not necessarily need to be two or more independent reactors but can also be comprised in a plant as independent reactors cells. In particular, the plant may be a plant in which several reactors are arranged or could be a single reactor composed of two or more reactor cells independently configurable among each other.

The invention is not limited to either singular reactors or reactor cells in a single reactor, but also combinations thereof are envisaged. Some of the two or more reactors could for example be singular reactors, while other of the two or more reactors could be reactor cells in a main reactor.

The present invention also offers the possibility of implementing existing plant with additional reactors and configuring these reactors in the way described in this application.

The reduced operation load of the plant can be arbitrary, however it has proven to be advantageous, if the operation load of the plant and thus the construction of the plant is based on a minimum load foreseen for the plant. The minimum load foreseen is defined as the amount of load which is expected to be available to the plant at and/or for any given period of time.

The minimum load foreseen therefore depends for example on environmental issues e.g. estimated and/or expected wind and sun presence in a future moment. Additionally, also socioeconomical issues can have an influence on the setting of the minimum load foreseen, such as potential energy crisis.

The minimum load foreseen can also be linked to load-following characteristics of the plant. If less energy output is required, the minimum load foreseen can be adapted avoiding useless energy waste. This creates a highly complex sustainable system with lower energy waste.

According to some embodiments the minimum load foreseen is based on input parameters received through environmental sensors outside and/or inside the plant, wherein the environmental sensors measure environmental parameters on which the load capacity of the plant is dependent.

Sensors can be chosen from a wide variety depending on what needs to be measured, although anemometers, solar light meters, temperature sensors and/or similar can be used. Other sensors may be arranged internally in the two or more reactors. These sensors could for example measure the amount of $CO_2$ inside the reactor, the pressure or the temperature. Also, metabolic parameters such as pH or ORP could be measured and could give important information regarding the state of the catalyst and the potentially available permutation period.

The input parameters can also be dependent on environmental predictions, like weather predictions (e.g. wind, sun, temperature, sea drift conditions). Sensors which describe the status of the reactor, such as wearing, temperature and the like are not excluded and are important to determine a minimum load foreseen. Furthermore, also sensor measuring characteristics of the catalyst are envisioned, such as sensor determining the adaptation of the catalyst to the present load, presence of $CO_2$ and/or similar.

According to some embodiments, the plant comprises a control and regulation unit, configured to obtain the plurality of data regarding the minimum load foreseen and/or other environmental data received for example from the sensors.

The control and regulation unit can be further configured to control the operation load of the two or more reactors and their permutation schedule as well as for example the overall operation load of the plant based on the data received.

According to some embodiment, the operation load of the plant can be based on the minimum load foreseen, if the minimum load foreseen is lower than a certain threshold value.

The threshold value is defined as value of load for which, if the minimum load foreseen is above that value, it is not advantageous to permutate the operation load of the two or more reactors of the plant. The threshold value can for example be set at ca. 95% of the optimal load capacity-meaning that, if for example the minimum load foreseen is just ca. 1% to ca. 4% lower than the operation load at optimal load capacity of the plant, the permutation of load does not occur. The threshold value can also be nearer to the optimal load capacity value, such as ca. 99.5% or ca. 99.9%.

This is however not limited, and highly dynamic plants are configured to continuously adjust their operation load depending on a continuous minimum load foreseen assessment as also envisaged in the present invention.

According to some embodiments of the present invention, when the optimal load capacity of the two or more reactors of the plant is evenly distributed, and when operation with reduced operation load of the plant is configured to be at least equal or higher than the optimal load capacity of one reactor as well as the two or more reactors are configured to have an operation load as follows:

For $i = 1$ $$OLR_1 = OLC_r \tag{1}$$

And for $i > 1$

-continued $$OLR_i = \begin{cases} OLC_r & \text{if } \left(OL_{reduced} - \sum_{i=1}^{i-1} OLR_i\right) > OLC_r \\ 0 & \text{if } \left(OL_{reduced} - \sum_{i=1}^{i-1} OLR_i\right) = 0 \\ OL_{reduced} \operatorname{mod}(OLC_r) & \text{else} \end{cases} \quad (2)$$

where

- N is the number of reactors in the reactor plant;
- i:={1, 2, . . . , N} is an index;
- $OLR_i$ is the operation load of the i-th reactor;
- $OL_{reduced}$ is the reduced operation load of the reactor plant; and
- $OLC_r$ is the optimal load capacity feeding capacity of each reactor.

Example A

A plant comprises three reactors (N=3; first, second and third reactors; i={1, 2, 3}). Supposing now that each reactor has an optimal load capacity of ca. 33% and that the operation with reduced operation load of the plant is ca. 50% of its optimal load capacity, then according to the above configurations of the reactors:

- The operation load of the first reactor (i=1) is ca. 33%, namely the optimal load capacity of the first reactor. Hence $OLR_1$=ca. 33%-according to (1).
- The reduced operation load of the plant (50%) minus the operation load of the first reactor (ca. 33%), is not higher than the optimal load capacity of the second reactor (ca. 50%-ca. 33%=ca. 17%<ca. 33%) and is not equal to zero (ca. 17% ca. 0%). Hence the third case in configuration (2), here above, applies and the operation load of the second reactor $OLR_2$ is (50 mod(33)), where mod is the modulo operator. Hence $OLR_2$=17% for i=2.
- The operation load of the third reactor $OLR_3$ is then ca. 0% (for i=3), meaning the third reactor is off. This is because ca. 50%-(ca. 33%+ca. 17%)=0, and hence the case described in the middle row of configuration (2) applies.

According to further embodiments of the invention, if the reduced operation load of the plant is configured to be lower than the optimal load capacity of each reactor of the two or more reactors, then the operation load of the first reactor is equal to the reduced operation load of the plant and the other reactors are off, as described here below:

$$\text{For } i = 1 \quad (1a)$$

$$OLR_1 = OL_{reduced}$$

$$\text{For } i > 1$$

$$OLR_i = 0. \quad (2a)$$

Example B

Hence in the above-described example with three reactors comprised in the plant, each having an optimal load capacity of ca. 33%, and setting a reduced operation load of the plant ($Min_{load}$) at 25%-then the first reactor has an operation load of ca. 25%, and the other two reactor have a rector operation load of ca. 0%.

The above configuration of the reactor according to either of the two embodiments, represents the operation load distribution of the reactors of the plant, during a first-time interval t=1. This operation load distribution is then periodically permutated according to the present invention, as described earlier.

This configuration of the reactors has proven to provide a plant which minimizes energy consumption and operational cost, which is flexible in cases of disturbances in load due to external factors and provides an operation system for the two or more rectors in which characteristics of the catalyst can be taken into consideration.

According to further embodiments of the present invention the periodical permutation of the one or more reactor is described as following matrix:

$$\begin{pmatrix} OLR_1 & OLR_2 & OLR_3 & \cdots & OLR_N \\ OLR_N & OLR_1 & OLR_2 & \cdots & OLR_{N-1} \\ OLR_{N-1} & OLR_N & OLR_1 & OLR_2 & \cdots \\ \vdots & \ddots & \ddots & \ddots & \ddots \\ OLR_2 & OLR_3 & \cdots & OLR_{N-1} & OLR_1 \end{pmatrix},$$

where every column corresponds to one reactor and every line represents the operation load distribution at different time intervals. The number of permutations required for the reactor to re-experience their initial load is equal to the number of reactors in the plant.

Example 3

In a plant with three reactors (R1, R2, R3), the permutation can be described according to the following matrix as:

$$R1 - R2 - R3$$

$$R2 - R3 - R1$$

$$R3 - R1 - R2$$

After the third permutation each reactor is fed with its initial load. If the biocatalyst is Archaea a complete permutation round occurs in a maximal possible time span of slightly less than 30 hours (one permutations after maximal slightly less than 10 hours). The invention is not limited to such permutations and any permutation scheme is envisaged. According to further embodiments permutation schedules are provided with forced permutations every 30 min, every hour, every 2, 3, 4, 5, 6, 7, 8 or 9 hours are envisaged.

According to some embodiments, a biocatalyst according to the present invention belongs to and is selected from the group of Archaea comprising the classes of Methanobacteria, Methanococci, Methanomicrobia, Methanonatronarchaeia, and Methanopyri each of these classes comprising a number of genera, wherein each genus is divided into families, each family encompassing a large number of known and extensively studied, in the meaning of classified, and unknown, in the meaning of unclassified, species.

According to some embodiments of the present invention, *Methanothermobacter*, and further *Methanothermobacter thermoautotrophicus*, *Methanothermobacter marburgensis* and/or mixtures thereof, and/or derivatives thereof revealed particularly easy to use as catalyst for the present invention.

Further, according to some embodiments of the present invention, *Methanothermus fervidus*, *Methanobrevibacter arboriphilicus*, *Methanococcus* and *Methanocaldococcus* sp., and further *Methanocaldococcus bathoardescens, Methanocaldococcus fervens, Methanocaldococcus indicus, Methanocaldococcus infernus, Methanocaldococcus jannaschii, Methanocaldococcus villosus, Methanocaldococcus vulcanius* and/or mixtures thereof, and/or derivatives thereof are particularly suitable to be adapted by the method of the present invention.

It is a further object of the invention to optimize efficiency even if specific resources are limited for a determined period of time.

The present invention hence also provides a method for regulating the operation of two or more reactors comprised in a reactor plant according the above-described embodiments during a period of operation with reduced operation load of the plant.

The method comprising the steps of:

a) Setting a reduced operation load for the reactor plant;

b) Operating the reactor plant at the determined reduced operation load by operating the two or more reactors at a respective operation load, in such a way that the sum of the operation load of the two or more reactors equals the set reduced operation load of step a); and c) Continuously permutating the operation load of the two or more reactors within periodically repeating time intervals, wherein the time intervals follow a defined and adaptable permutation schedule in dependency of the metabolic characteristics of the catalyst used in the two or more reactors.

The method comprises as a first step setting a reduced operation load at which the reactor plant will operate. Setting the reduced operation load can be based according to some embodiments on a minimum load foreseen for the plant.

According to further embodiments of the present method, step b) comprises the step of operating the least number of reactors possible. Operating the least number of reactors necessary means in particular that, if possible, at least one reactor of the two or more reactors operates at its optimal load capacity.

With the catalyst being load sensitive and with step c) of the permutation of operation loads, it becomes possible to maintain the catalyst in each reactor in a state of high load adaptation-therefore maximizing the quality and quantity of output products and optimizing i.e. reducing ramp-up times.

The interval between each permutation is set depending on the metabolic characteristics of the load sensitive catalyst used and may lead to a catalyst specific permutation schedule.

According to an embodiment of the present method the reduced operation load of the plant is based on a minimum load foreseen for the plant. The minimum load foreseen can be set through the determination and evaluation of environmental parameters captured by sensor arranged in and/or outside of the plant and in particular inside and/or outside the individual reactor of the plant.

According to the data provided by the environmental parameter obtained through different environmental sensors, which can for example comprise pressure sensors, temperature sensors, flow sensors and similar, but are not limited to these, the load foreseen is determined. This means that a predictive behaviour of the plant based on environmental data is determined and the operation of the plant and thus of the two or more reactor is set accordingly.

According to a further embodiment step b) is chosen according to the following configuration scheme:

For $i = 1$ $$OLR_1 = OLC_r \tag{1}$$

And for $i > 1$ $$OLR_i = \begin{cases} OLC_r & \text{if } \left(OL_{reduced} - \sum_{i=1}^{i-1} OLR_i\right) > OLC_r \\ 0 & \text{if } \left(OL_{reduced} - \sum_{i=1}^{i-1} OLR_i\right) = 0 \\ OL_{reduced}\text{mod}(OLC_r) & \text{else} \end{cases} \tag{2}$$

where

N is the number of reactors in the reactor plant;

i:={1, 2, . . . , N} is an index;

$OLR_i$ is the operation load of the i-th reactor;

$OL_{reduced}$ is the reduced operation load of the reactor plant; and $OLC_r$ is the optimal load capacity feeding capacity of each reactor.

Furthermore, the permutation optimizes the periods in which minimal power sources are available to the plant and guarantees a low usage of energy while maintain a high output of the plant. As such it renders the system more efficient and environmentally friendlier than known systems of the prior art.

According to a further embodiment, step c) is performed only if the predefined reduced operation load of the plant is lower than a first threshold value. If for example in a two-reactor example, the reduced operation load of the plant is about 99% of the optimal load capacity, it might not be necessary to permutate the loads, as the catalyst in both reactor stays adapted to high load (one reactor e.g. operating with 50% operation load and the other with 49%). The first threshold value could therefore be defined such that permutation occur only if the catalyst in one reactor cannot be maintained at high load adaptation.

According to an even further embodiment step a) is performed only if the minimum load foreseen is lower than a second threshold value. The second threshold value is defined as value for which, if the minimum load foreseen is above, it is not advantageous, energy wise, to modify the operation load of the two or more reactors of the plant. The second threshold value can for example be set at ca. 95% of the optimal load capacity-meaning that, if for example, the minimum load foreseen is just ca. 1% to ca. 4% lower than the operation load at optimal load capacity of the plant, the operation load of the reactor is not adapted. The second threshold value can also be nearer to the optimal load capacity value, such as ca. 99.5% or ca. 99.9%.

According to the present invention also a computer implemented method for regulating the operation load of two or more reactors comprised in a plant is provided.

The plant is configured according to the above embodiments.

According to the invention the method comprises the steps of:

a) Determining a reduced operation load for the plant for a given period based on an environmental data set obtained by one or more environmental sensors arranged inside and/or outside of the plant;

b) Determining an operation load distribution of the two or more reactors of the plant based on the reduced operation load for the plant;

c) Operating the two or more reactors according to the operation load distribution; and d) Periodically permutating the operation load of the two or more reactors based on a permutation command.

Optionally, the computer implemented invention can comprise also following steps after step c) above:

c1) Continuously monitoring catalyst parameters inside the reactors though data input received by means of measurements; and c2) Generating a permutation command when the catalyst in at least one reactor is approaching a low load adaptation based on the catalyst parameters.

The computer implemented method is hence capable of assessing environmental data being fed to the control unit of the reactor system through sensors connected to the plant and accordingly manage and/or control the operation load of the plant and of the two or more reactors in the plant.

The environmental data set comprises data of the present environmental situation such as pressure, temperature, wind and/or solar power and similar. The environmental data set also comprises future predicted environmental data, predicting an environmental situation. With the data set it becomes possible to determine a minimum load foreseen for the plant. The environmental dataset can be provided continuously such as to have a continuous determination of the minimum load foreseen.

Through the continuous evaluation of technical environmental data, the operation of the plant can be optimized with respect to prior art plants. In particular, it is so possible to minimise the energy input required for the plant, while maintaining equal or higher outputs, by regulating the operation of the plant based on the energy input available at a certain time.

According to an embodiment of step b) of the present method, a reduced operation load scheme of the plant based on the minimum load foreseen for the plant is determined and the required operation load of the two or more reactors of the plant corresponding to the reduced operation load scheme of the plant is determined.

The reduced operation load scheme comprises data sets indicating the reduced operation load of the plant required to be in line with the minimum load foreseen of the plant. The operation load of the two or more reactors is thus the determined load of the two or more reactors required to obtain the reduced operation load of the plant.

According to an embodiment of step c) of the method when the expected minimum load foreseen occurs, the plant is operated at reduced operation load according to the determined reduced operation load scheme. According to some embodiments, operating the plant according to the reduced operation load scheme means operating the two or more reactors with an operation load which is such that the sum of the operation load of the two or more reactors equals the reduced operation load of the plant.

In step d) of the method, the operation load of the two or more reactors is continuously permutated according to a permutation schedule and thus, within a time frame, meaning that after a certain time interval, the reactor changes among each other their operational load, maintaining however the sum of the operation load equal. The time frame or permutation schedule is chosen such as to maintain the catalyst in adaptation to full load capacity of the plant.

According to some embodiments of the present invention, the operation of the two or more reactors occurs such that at least one of the two or more reactors operates at full load capacity, and/or at least one of the two or more reactor is shut off.

This is particularly advantageous as it minimizes wearing of the reactors, it minimizes ramp up times, because the catalyst is maintained at full load capacity and the ramp down of one reactor is compensated by the ramp up of another reactor.

According to some embodiments of the computer implemented invention the calculation of the operation load of the two or more reactors in a reduced operation load moment of the plant is given by the following formula:

$$\text{For } i = 1$$

$$OLR_1 = OLC_r$$

$$\text{And for } i > 1$$

$$OLR_i = \begin{cases} OLC_r & \text{if } \left(OL_{reduced} - \sum_{i=1}^{i-1} OLR_i\right) > OLC_r \\ 0 & \text{if } \left(OL_{reduced} - \sum_{i=1}^{i-1} OLR_i\right) = 0 \\ OL_{reduced}\,\mathrm{mod}(OLC_r) & \text{else} \end{cases}$$

where

N is the number of reactors in the reactor plant;

i:={1, 2, . . . , N} is an index;

$OLR_i$ is the operation load of the i-th reactor;

$OL_{reduced}$ is the reduced operation load of the reactor plant; and $OLC_r$ is the optimal load capacity feeding capacity of each reactor.

According to the present invention also a computer program is provided, the computer program comprising instructions which, when the program is executed by a computer, cause the computer to carry out the methods as described above.

According to the present invention also computer readable media are provided, the computer readable media comprising instructions which, when executed by a computer, cause the computer to carry out the methods as described above The following invention is further explained by means of the following detailed description of exemplary embodiment and examples.

FIG. 1 shows a schematic plant according to an embodiment of the present invention;

FIG. 2*a* shows an operation load scheme for a plant with two reactors during operation with reduced operation load of the plant;

FIG. 2*b* shows an operation load scheme for a plant with two reactors during a further operation with reduced operation load of the plant;

FIG. 3*a* shows an operation load scheme for a plant with three reactors during the operation with reduced operation load of the plant as in FIG. 2*a;*

FIG. 3*b* shows an operation load scheme for a plant with three reactors during the operation with reduced operation load of the plant as in FIG. 2*b;*

As can be seen from FIG. 1, the plant 10 according to the following exemplary embodiment comprises three reactors, 12*a*, 12*b*, 12*c*. The reactors are connected in parallel and can hence function simultaneously and independently.

Each reactor comprises environmental sensors 20*a*, 20*b*, 20*c* which collect environmental data inside the respective reactor, such as temperature, amount of CO2, pH Value, quantity of load and similar. The collected data is sent to a control unit 40, configured to collect and process incoming environmental data from the environmental sensors 20*a*, 20*b*, 20*c*.

The plant 10 of the present example receives input energy (not shown) from a windfarm 30. Further environmental sensors 32 are arranged at the windfarm 30. The sensors 32 are connected to the control unit 40 and feed the control unit 40 with data regarding the present and the predicted situation at the windfarm 30 (e.g. wind force, wind direction, energy generation per windmill, etc.).

The control unit 40 is configured to process all the incoming data and determine a minimum load foreseen for the plant 10 and for the three reactors 12*a*,12*b*, 12*c*. In this way, when energy supply from the windfarm 30 is scarce due for example to a lack of wind, the control unit 40 can set the operation load of the plant accordingly and the distribution of operation load of the reactors.

If the load available through the windfarm 30 is limited and the plant 10 is required to operate with a reduced operation load, then the plant 10 is configured to permutate the loads of the reactors 12*a*, 12*b*, 12*c* at periodical intervals. The intervals depend on the catalyst used.

The invention is not limited to this embodiment. The energy sources are not limited to the windfarm 30 and the sensor are not limited as being arranged either at the energy source or inside the reactors.

The tables in FIGS. 2*a*, 2*b* relate to a plant comprising two reactors, namely a first reactor 1 and a second reactor 2. The tables show the operation load during a period of operation with reduced load of the plant. The reactors in this example have an evenly distributed optimal load capacity of 50% each. Hence when both reactors receive respectively 50% of the load of the plant, the reactions in the reactor are substantially optimal.

The table of FIG. 2*a*, shows for example, a situation in which the reduced operation load of the plant is set at 50% of its optimal load capacity of 100%.

In the following example the operation load distribution scheme during reduced operation load of the plant, is such that at a time t=1, the first reactor 1 operates with 50% operation load. Hence the whole load at disposal of the plant is fed to reactor 1. Reactor 1 is hence operating at its optimal load capacity and hence exhibits nearly substantially optimal reactions. The catalyst of reactor 1 remains adapted to high loads.

The second reactor 2, instead is fed with 0% load. The catalyst of the second reactor, however, although not receiving any load, remains adapted to high load.

Before the catalyst of the second reactor tends to adapt to low loads, the loads of the reactors are permutated (t=2) and the first reactor experiences 0% load and the second reactor 2 receives 50% load (it's optimal load capacity).

The catalyst of the second reactor 2, which was adapting to low loads, receives the optimal quantity of load and hence remains in a high load adaptation. Reactor 2 hence experiences nearly instantaneous ramp-up rates and quick substantial optimal reactions.

According to a further example, shown in the table of FIG. 2*b*, the reduced operation load of the plant is 75%. This means that according to the present invention the first reactor 1 operates with 50% load (being its optimal load capacity) and the second reactor 2 operates at 25% operation load.

At time t=2, the loads permutate, and the first reactor 1 operates with 25% working, while the second reactor 2 operates at 50% operation load.

As can be seen for this example, the cumulative operation load of the reactors of the plant corresponds always the reduced operation load of the plant, given by the minimum load foreseen. During the permutation, one reactor must ramp down while the other reactor ramps up. In this way no energy is lost, and a load of 50% or 75% respectively for the plant is constantly achieved.

In these examples, at least one reactor operates constantly with its optimal load capacity, such that the catalyst in that reactor is kept at high load adaptation.

FIGS. 3*a* and 3*b* show a similar situation of the respective FIGS. 2*a* and 2*b*, but with a plant comprising three reactors, e.g. a first reactor 1, a second reactor 2, a third reactor 3. Each reactor has an optimal load capacity of ca. 33%.

FIG. 3*a*, shows a situation in which the reduced operation load of the plant is set at 50%.

At time t=1, the first reactor 1 operates with 33% operation load (being its optimal load capacity), the second reactor 2 operates with 17% and the third reactor 3 with 0% load. Although having different load percentages fed to the catalyst, the catalyst in the different reactors remain adapted to high loads.

After a first permutation at t=2 the first reactor 1 receives 0% load, the second reactor 2 operates with 33% operation load and the third reactor 3 operates with 17%. The permutation occurred before the catalyst of the reactors 1 and 3 could adapt to low loads, hence also during t=2, all reactors comprise catalyst adapted to high loads and the ramp up time of the reactors experiencing again higher loads is rapid.

After a further permutation at t=3 the first reactor 1 operates with 17%, the second reactor 2 with 0% and the third reactor 3 operates with 33% operation load. Again, the permutation occurred before the catalyst of the reactors 1 and 2 could adapt to low loads, hence also during t=3, all reactors comprise catalyst adapted to high loads and the ramp up time of the reactors experiencing again higher loads is rapid.

FIG. 3*b*, shows a situation in which the reduced operation load of the plant is set at 75%.

At time t=1, the first reactor 1 operates with 33% operation load (being its optimal load capacity), the second reactor 2 operates with 33% (being also its optimal load capacity) and the third reactor 3 with 9% load. Although having different load percentages fed to the catalyst, the catalyst in the different reactors is adapted to high loads.

After a first permutation at t=2 the first reactor 1 receives 9% load, the second reactor 2 operates with 33% operation load and the third reactor 3 operates with 33%. The permutation occurred before the catalyst of reactor 3 could adapt to low loads, hence also during t=2, all reactors comprise catalyst adapted to high loads and the ramp up time of the reactors experiencing again higher loads is rapid.

After a further permutation at t=3 the first reactor 1 operates with 33%, the second reactor 2 with 9% and the third reactor 3 operates with 33% operation load. Again, the permutation occurred before the catalyst of the reactors 1 could adapt to low loads, hence also during t=3, all reactors comprise catalyst adapted to high loads and the ramp up time of the reactors experiencing again higher loads is rapid.

As one of the major advantages of the present invention it is seen, that the efficient use of input energy, the ongoing control of the reactor exploitation and the exploitation of the microbial capabilities to overcome latency periods together with all the above mentioned advantages of the invention do all play an essential part in the calculation of the product carbon footprint as well as the life-cycle assessment (LCA) of the reactor and consequently in a calculation of the global warming potential and the environmental impact.

A product carbon footprint is a mean to measure of direct and indirect greenhouse gas (GHG) emissions associated with all activities in the goods life cycle. Accordingly, the life-cycle assessment (LCA) can be used to calculate such carbon footprints. Together LCA focusses on, e.g., GHG emissions that has an advantageous effect on climate change and the global warming potential (GWP) itself.

In other words, the design of the reactor according to the invention and the new and inventive method to optimize and regulate the reactor plants in order to optimize the production capacity of a load sensitive catalyst does result in an improved carbon footprint of the product, e.g. the methane produced according to one embodiment of the invention.

The current invention demonstrates benefits for the environment through its sensible use of resources, thereby making a green technology such as a methanation process and/or synthesis process regarding other products even more environmentally friendly. This results in a substantially improved carbon footprint for the product produced in the disclosed reactor and according to the disclosed method and thus an improved environmental impact.

The invention claimed is:

1. A reactor plant, comprising two or more reactors connected in parallel with each other, wherein the two or more reactors comprise a load sensitive biocatalyst comprising hydrogenotrophic methanogen suitable to be used alone or in co-culture in a methanation process, wherein each reactor has an optimal load capacity, wherein the sum of the optimal load capacities of the two or more reactors corresponds to an optimal load capacity of the reactor plant;

wherein the reactor plant is configured to operate with an operation load, wherein the operation load of the reactor plant is the optimal load capacity of the plant or a reduced operation load;

wherein each reactor is configured to operate with an operation load, wherein the combined operation load of the two or more reactors is equal to the operation load of the reactor plant, and wherein the reactor plant comprises a control and regulation unit configured to control the operation load of the two or more reactors, characterized in that during operation of the reactor plant with a reduced operation load, the two or more reactors are configured by the control and regulation unit to continuously permutate their respective operation loads within periodically repeating time intervals, dependent on the metabolic characteristics of the biocatalyst, wherein the control and regulation unit are configured to continuously adjust the operation load of the two or more reactors depending on a continuous assessment of the minimum load foreseen based on input parameters received through environmental sensors outside and/or inside of the plant, and wherein the load encompasses energy and substrate(s) together and/or in singularity needed for the maintenance and reaction of the biocatalyst.

2. The reactor plant according to claim 1, wherein the optimal load capacity of the plant is evenly distributed between the two or more reactors.

3. The reactor plant according to claim 1, wherein the two or more reactors are reactor cells in a main reactor.

4. The reactor plant according to claim 1, wherein the environmental sensors measure environmental parameters on which the future operation load of the plant is dependent.

5. The reactor plant according to claim 1, wherein the control and regulation unit is configured to obtain a plurality of data regarding the minimum load foreseen and/or other environmental data, and to control the operation load of the two or more reactors and their permutation schedule.

6. The reactor plant according to claim 2, wherein if the reduced operation load of the plant is configured to be at least equal or higher than the optimal load capacity of each reactor, the two or more reactors are configured to have an operation load as follows:

$$\text{For } i = 1$$

$$OLR_1 = OLC_r; \tag{1}$$

$$\text{and for } i > 1$$

$$OLR_i = \begin{cases} OLC_r & \text{if } \left(OL_{reduced} - \sum_{i=1}^{i-1} OLR_i\right) > OLC_r \\ 0 & \text{if } \left(OL_{reduced} - \sum_{i=1}^{i-1} OLR_i\right) = 0 \\ OL_{reduced} \operatorname{mod}(OLC_r) & \text{else} \end{cases}; \tag{2}$$

where

N is the number of reactors in the reactor plant;

i:={1, 2, . . . , N} is an index;

$OLR_i$ is the operation load of the i-th reactor;

$OL_{reduced}$ is the reduced operation load of the reactor plant; and $OLC_r$ is the optimal load capacity feeding capacity of each reactor.

7. The reactor plant according to claim 1, wherein the periodical permutation of the one or more reactors is described as:

$$\begin{pmatrix} OLR_1 & OLR_2 & OLR_3 & \cdots & OLR_N \\ OLR_N & OLR_1 & OLR_2 & \cdots & OLR_{N-1} \\ OLR_{N-1} & OLR_N & OLR_1 & OLR_2 & \cdots \\ \vdots & \ddots & \ddots & \ddots & \ddots \\ OLR_2 & OLR_3 & \cdots & OLR_{N-1} & OLR_1 \end{pmatrix},$$

where every column corresponds to one reactor and every line represents the operation load distribution at different time intervals.

* * * * *